United States Patent [19]
Brenner et al.

[11] Patent Number: 5,286,653
[45] Date of Patent: Feb. 15, 1994

[54] METHOD FOR DETECTING THE GAMMA, DELTA T CELL RECEPTOR

[75] Inventors: Michael B. Brenner, Ashland; Jack L. Strominger, Lexington; Jonathan Seidman, Milton; Stephen H. Ip, Framingham; Michael S. Krangel, Newtonville, all of Mass.

[73] Assignees: T Cell Diagnostics, Inc., Cambridge; Dana Farber Cancer Institute; President & Fellows of Harvard College, both of Boston, all of Mass.

[21] Appl. No.: 881,825

[22] Filed: Jul. 3, 1986

[51] Int. Cl.$^5$ .......................................... G01N 33/566
[52] U.S. Cl. .................................. 436/501; 436/548; 436/506; 435/7.1; 435/7.24; 435/240.2; 435/172.2; 530/388.22; 530/388.75; 530/389.6; 935/101
[58] Field of Search ................ 436/548, 501, 506, 813; 435/7, 172.2, 240.27, 7.1, 7.23; 530/387

[56]   References Cited
U.S. PATENT DOCUMENTS

| | | | |
|---|---|---|---|
| 4,444,744 | 4/1984 | Goldenberg | 424/1.1 |
| 4,550,086 | 10/1985 | Reinherz et al. | 436/548 |
| 4,713,332 | 2/1984 | Mak | 435/69.1 |
| 4,845,026 | 7/1989 | Kung et al. | 435/7 |
| 4,874,845 | 6/1984 | Saito et al. | 530/395 |

OTHER PUBLICATIONS

Sims et al, The EMBO Journal, vol. 5, No. 6, 1986, pp. 1245-1252.
Elsen et al, Proc. Natl. Acad. Sci. USA, vol. 83, May 1986, pp. 2944-2948.
LeFranc et al, Cell, vol. 45, Apr. 1986, pp. 237-246.
Reilly et al., 1986, Nature 321:878-880.
Rupp et al., 1986, Nature 321:876-878.
LeFranc et al., 1986, Proc. Natl. Acad. Sci. U.S.A. 83:9596-9600.
MacLeod et al., 1986, Proc. Natl. Acad. Sci. U.S.A. 83:6989-6993.
Royer et al., 1984, J. Exp. Med. 160:947-952.
Sevier et al, Clin. Chem, vol. 27/11, pp. 1797-1806, 1981.
Dialynas et al, PNAS, USA, vol. 83, Apr. 1986, pp. 2619-2623.
Quertermous et al, Science, vol. 231, Jan. 1986, pp. 252-255.
Murre et al, Nature, vol. 316, Aug. 8, 1985, pp. 549-552.
Hopp et al, PNAS, vol. 78, 1981, pp. 3824-3828.
Kyte et al, J. Mol. Biol., vol. 157, 1982, pp. 105-132.
Allison et al., J. Immunol. 129, 2293-2300 (1982).
Kappler et al., Cell 35, 295-302 (1983).
Acuto et al., J. Exp. Med. 158, 1368-1373 (1983).
Haskins et al., J. Exp. Med. 157, 1149-1169 (1983).
Acuto et al., Cell 34, 717-726 (1983).
Samelson and Schwartz, Immunological Reviews 81, 131-144 (1984).
Hedrick et al., Nature 308, 153-158 (1984).
Yanagi et al., Nature 308, 145-149 (1984).
Saito et al., Nature 312, 36-40 (1984).
Sim et al., Nature 312, 771-775 (1984).
Chien et al., Nature 312, 31-35 (1984).
Siu et al., Cell 37, 393-401 (1984).
Patten et al., Nature 312, 40-46 (1984).
Yoshikai et al., Nature 312, 521-524 (1984).

(List continued on next page.)

Primary Examiner—Robert J. Hill, Jr.
Assistant Examiner—Laurie Scheiner
Attorney, Agent, or Firm—Pennie & Edmonds

[57] ABSTRACT

The present invention provides purified polypeptides which comprise at least a portion of a δT cell receptor polypeptide, a γT cell receptor polypeptide or a γ,δ T cell receptor complex. Substances capable of forming complexes with these polypeptides are also provided. Additionally, methods for detecting T cells which have within them or on their surfaces a polypeptide of the present invention are provided. Moreover, methods for diagnosing immune system abnormalities are provided which comprise measuring in a sample from a subject the number of T cells which have within them or on their surfaces a polypeptide of the present invention.

60 Claims, 4 Drawing Sheets

OTHER PUBLICATIONS

Yanagi et al., Proc. Natl. Acad. Sci. U.S.A. 82, 3430–3434 (1985).
Hedrick et al., Proc. Natl. Acad. Sci. U.S.A. 82, 531–535 (1985).
Becker et al., Nature 317, 430–434 (1985).
Tonegawa, Scientific American, pp. 122–131, Oct., 1985.
Yague et al., Cell 42, 81–87 (1985).
Blanckmeister et al., J. Exp. Med. 162:851–863 (1985).
Dembic et al., Nature 320, 232–238 (1986).
Saito et al., Nature 309, 757–762 (1984).
Kranz et al., Nature 313, 752–755 (1985).
Snodgrass et al., Nature 315, 232–233 (1985).
Lefranc and Rabbitts, Nature 316, 464–466 (1985).
Heilig et al., Nature 317, 68–70 (1985).
Hayday et al., Cell 40, 259–269 (1985).
Iwamoto et al., J. Exp. Med. 163, 1203–1212 (1986).
Zauderer et al., J. Exp. Med. 163, 1314–1318 (1986).
Caccia et al., Cell 37, 1091–1099 (1984).
Kranz et al., Science 227, 941–944 (1985).
Brenner et al., J. Exp. Med. 160, 541–551 (1984).
Spits et al., J. Immunol. 135, 1922–1928 (1985).
Reinherz et al., Cell 30, 735–743 (1982).
Borst et al., J. Biol. Chem. 258, 5135–5141 (1983).
Reinherz et al., Proc. Natl. Acad. Sci. U.S.A. 80, 4104–4108 (1983).
Meuer et al., J. Exp. Med. 157, 705–719 (1983).
Oettgen et al., J. Biol. Chem. 259, 12039–12048 (1984).
Weiss and Stobo, J. Exp. Med. 160, 1284–1299 (1984).
Allison and Lanier, Nature 314, 107–109 (1985).
Brenner et al., Cell 40, 183–190 (1985).
Van den Elsen et al., Proc. Natl. Acad. Sci. U.S.A. 82, 2920–2924 (1985).
Ohashi et al., Nature 316, 606–609 (1985).
Krawinkel et al., Cold Spring Harb. Symp. Quant. Biol. 4, 285–294 (1976).
Binz and Wigzell, Cold Spring Harb. Symp. Quant. Biol. 4, 275–284 (1976).
Binz and Wigzell, J. Exp. Med. 154, 1261–1278 (1981).
Kung et al., Int. J. Dermat. 22, 67–73 (1983).
Krensky and Clayberger, Transplantation 39(4):339–348 (1985).
de la Hera et al., Proc. Natl. Acad. Sci. U.S.A. 82, 6268–6271 (1985).
Levin, L. S., et al., J. Pediatrics 90(1), 55–61 (1977).
Griscelli et al., (1980), in Primary Immunodeficiencies, Seligmann, M. and Hitzig, W. H., eds., Elsevier/North-Holland, pp. 499–503.
Hadam, et al., (1984), in Progress in Immunodeficiency Research and Therapy I, Griscelli, C. and Vossen, J., eds., Elsevier Science Publishers B.V., pp. 43–50.
Chan and Takei, J. Immunol. 136(4), 1346–1353 (1986).

METHOD FOR DETECTING THE GAMMA, DELTA T CELL RECEPTOR

This invention was supported by several NIH grants, and the Government has certain rights to the invention.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Understanding T cell recognition of antigen and the restriction of the process by major histocompatibility complex (MHC) encoded antigens has been an important goal in immunology. A major step forward occurred with the immunochemical identification of clone specific disulfide-linked heterodimers on T cells, composed of subunits termed T cell antigen receptors (TCR) $\alpha$ and $\beta$. The TCR $\alpha$ and $\beta$ subunits have a relative molecular mass ($M_r$) of approximately 50,000 and 40,000 daltons, respectively (1, 2, 3). Genes that rearrange during T cell ontogeny and encode the TCR $\beta$ (4, 5) and TCR $\alpha$ (6, 7, 8) subunits were isolated either by subtractive hybridization or by probing with oligonucleotides.

A unique feature of the human TCR $\alpha,\beta$ was the observed comodulation (2), coimmunoprecipitation (9, 10) and required coexpression (11) of the TCR $\alpha,\beta$ molecules with the T3 glycoprotein, which suggested that these two structures were related. Subsequently, the direct physical association of the two protein complexes was demonstrated by chemically cross-linking the TCR $\alpha$, $\beta$ molecules to the T3 glycoprotein and identifying the components of the cross-linked complex as the TCR $\beta$ subunit and the T3 glycoprotein ($M_r$ 28,000) subunit (12). A T3 counterpart is similarly associated with murine TCR $\alpha,\beta$ (13, 14).

A third gene that rearranges in T cells, designated TCR $\gamma$, has been identified in mouse (15, 16, 17) and in man (18, 19). However, there are major differences between the human and mouse TCR $\gamma$ gene in terms of its genetic structure; for example, the cDNA of the human TCR $\gamma$ gene indicates five potential sites for N-linked glycosylation in the TCR $\gamma$ gene (36) product, which contrasts with the notable absence of such sites in the murine TCR $\gamma$ gene (15). Thus, the human TCR $\gamma$ gene product will have a high molecular weight which is not predictable from its genetic sequence.

The TCR $\gamma$ gene rearrangements occur in lymphocytes with suppressor-cytotoxic as well as helper phenotypes and may produce a large number of TCR $\gamma$ chains (18, 19, 20, 21, 22, 23). However, the function of the TCR $\gamma$ gene is unknown. Furthermore, neither the protein encoded by the TCR $\gamma$ gene nor its possible association with other structures (as occurs with TCR $\alpha,\beta$ and T3 glycoproteins) have been defined. In humans, the multiple glycosylation sites render it impossible to predict with accuracy the nature and size of the TCR $\gamma$ polypeptide structure. Additionally, the published literature does not teach or suggest the utility of TCR $\gamma$ with regard to diagnosing, monitoring or staging human diseases.

It appears increasingly likely that the TCR $\alpha$, $\beta$ molecule alone determines both antigen recognition and MHC restriction on at least some T cells (24, 25). However, it is not clear that TCR $\alpha,\beta$ accounts for the process of T cell selection during T cell ontogeny or for all antigen specific recognition by mature T cells. For example, suppressor T lymphocytes remain an enigma; in some cases they delete or fail to rearrange TCR $\beta$ genes (26,27). Thus, it is of great importance to determine if a second T cell receptor exists, to define its structure (particularly with regard to the possible use of the TCR $\gamma$ gene product) and ultimately to understand what function or functions it serves.

SUMMARY OF THE INVENTION

The present invention provides a purified polypeptide which comprises at least a portion of a $\delta$T cell receptor polypeptide. Additionally, a substance capable of specifically forming a complex with at least one $\delta$T cell receptor polypeptide is provided.

Also provided is a method for detecting T cells, each of which has a $\delta$T cell receptor polypeptide. This method comprises contacting a sample which contains T cells with substances capable of forming complexes with $\delta$T cell receptor polypeptides so as to form cellular complexes between the substances and the $\delta$T cell receptor polypeptides. These cellular complexes are detected and thereby T cells, each of which has a $\delta$T cell receptor polypeptide, are detected.

The invention further provides a method for diagnosing an immune system abnormality in a subject. This method comprises determining the number of T cells in a sample from the subject and contacting the sample with substances capable of forming complexes with at least one $\delta$T cell receptor polypeptide so as to form cellular complexes between the substances and the $\delta$T cell receptor polypeptides. The percentage of T cells in the sample which have a $\delta$T cell receptor polypeptide is determined and compared with the percentage of T cells which have a $\delta$T cell receptor polypeptide in a sample from a normal subject who does not have the immune system abnormality. A difference in the percentage of T cells so determined would be indicative of the immune system abnormality.

A further method for diagnosing an immune system abnormality in a subject is provided by the present invention. This method comprises determining the number of $\delta$T cell receptor polypeptide bearing T cells in a sample from the subject and determining the amount of $\delta$T cell receptor polypeptides in the $\delta$T cell receptor bearing T cells. The amount of $\delta$T cell receptor polypeptides so determined is compared with the amount of $\delta$T cell receptor polypeptides in an equal number of $\delta$T cell receptor polypeptide bearing T cells in a sample from a normal subject who does not have the immune system abnormality. A difference in the amount so determined would be indicative of the immune system abnormality.

A further method for diagnosing an immune system abnormality in a subject is provided. This method comprises determining in a sample from the subject the number of T cells which have a $\delta$T cell receptor polypeptide and the number of T cells consisting of the group of T cells which have one of the surface markers T4, T8 and $\alpha,\beta$2 T cell receptor. The numbers of T cells so determined are compared with the number of T cells which have a $\delta$T cell receptor polypeptide and the number of T cells in the group which have the same surface marker as the group of T cells determined in the sample from the subject, in a sample from a subject who does not have the immune system abnormality. A difference in the number of T cells so determined which have a δT cell receptor polypeptide relative to the number of T cells in the group so determined would be indicative of the immune system abnormality.

The present invention also provides a purified polypeptide which comprises at least a portion of a γT cell receptor polypeptide. Additionally, a substance capable of specifically forming a complex with at least one γT cell receptor polypeptide is provided. Furthermore, a method for detecting T cells, each of which has a γT cell receptor polypeptide is provided. This method comprises contacting a sample which contains T cells with substances capable of forming complexes with γT cell receptor polypeptides so as to form cellular complexes between the substances and the γT cell receptor polypeptides. These cellular complexes are detected and thereby T cells, each of which has a γT cell receptor polypeptide, are detected.

A further method for diagnosing an immune system abnormality in a subject is provided by the present invention. This method comprises determining the number of T cells in a sample from the subject and contacting the sample with substances capable of forming complexes with at least one γT cell receptor polypeptide so as to form cellular complexes between the substances and the γT cell receptor polypeptides. The percentage of T cells in the sample which have a γT cell receptor polypeptide is determined and compared with the percentage of T cells which have a γT cell receptor polypeptide in a sample from a normal subject who does not have the immune system abnormality. A difference in the percentage of T cells so determined would be indicative of the immune system abnormality.

Still another method for diagnosing an immune system abnormality is provided. This method comprises determining the number of γT cell receptor polypeptide bearing T cells in sample from the subject and the amount of γT cell receptor polypeptides in a the γT cell receptor polypeptide bearing T cells. The amount of γT cell receptor polypeptides so determined is compared with the amount of γT cell receptor polypeptides in an equal number of γT cell receptor polypeptide bearing T cells in a sample from a normal subject who does not have the immune system abnormality. A difference in the amount so determined would be indicative of the immune system abnormality.

Yet another method is provided by the present invention for diagnosing an immune system abnormality in a subject. This method comprises determining in a sample from the subject the number of T cells which have a γT cell receptor polypeptide and the number of T cells consisting of the group of T cells which have one of the surface markers T4, T8 and a α,β T cell receptor. The numbers of T cells so determined are compared with the number of T cells which have a γT cell receptor polypeptide and the number of T cells in the group which have the same surface marker as the group of T cells determined in the sample from the subject, in a sample from a subject who does not have the immune system abnormality A difference in the number of T cells so determined which have a γT cell receptor polypeptide relative to the number of T cells in the group so determined would be indicative of the immune system abnormality.

The invention further provides a purified complex which comprises at least a portion of a δT cell receptor polypeptide and at least a portion of a γT cell receptor polypeptide. Also provided are substances capable of specifically forming a complex with at least one γ, δT cell receptor complex. Moreover, a method for detecting T cells, each of which has a γ, δT cell receptor complex, is provided. This method comprises contacting a sample which contains T cells with substances capable of forming complexes with γ, δT cell receptor complexes so as to form cellular complexes between the substances and the γ,δT cell receptor complexes. These cellular complexes are detected and thereby T cells, each of which has a γ, δT cell receptor complex, are detected.

Still further, the present invention provides another method for diagnosing an immune system abnormality in a subject. This method comprises determining the number of T cells in a sample from the subject and contacting the sample with substances capable of forming complexes with at least one γ, δT cell receptor complex so as to form cellular complexes between the substances and the γ, δT cell receptor complexes. The percentage of T cells which have a γ, δT cell receptor complex is determined and compared with the percentage of T cells which have a γ, δT cell receptor complex in a sample from a normal subject who does not have the immune system abnormality. A difference in the percentage of T cells so determined would be indicative of the immune system abnormality.

The invention provides yet another method of diagnosing an immune system abnormality in a subject. This method comprises determining the number of γ, δT cell receptor complex bearing T cells in a sample from the subject and the amount of γ,δT cell receptor complexes in the γ, δT cell receptor complex bearing T cells. The amount of γ,δT cell receptor complexes so determined is compared with the amount of γ,δT cell receptor complexes in an equal number of γ,δT cell receptor complex bearing T cells in a normal subject who does not have the immune system abnormality. A difference in the amount so determined would be indicative of the immune system abnormality.

Yet another method for diagnosing an immune system abnormality is provided by the present invention. This method comprises determining in a sample from the subject the number of T cells which have a γ,δT cell receptor complex and the number of T cells consisting of the group which have one of the surface markers T4, T8 and a α,βT cell receptor complex. The numbers of T cells so determined are compared with the number of T cells which have a γ, δT cell receptor complex and the number of T cells in the group which have the same surface marker as the group of T cells determined in the sample from the subject, in a sample from a subject who does not have the immune system abnormality. A difference in the number of T cells so determined which have a γ, δT cell receptor complex relative to the number of T cells in the group would be indicative of the immune system abnormality.

BRIEF DESCRIPTION OF THE FIGURES

A. Lane 1: Control antibody, normal mouse serum.
Lane 2: Anti-framework TCR α,β monoclonal antibody (βF1).

B. Lane 1: Control antibody, normal mouse serum. Lane 2: Anti-T3 monoclonal antibody (UCHT-1). Lane 3: Anti-framework TCR α,β monoclonal antibody (WT31).

C. Three dimensional display of flow cytometry analysis of normal adult peripheral blood lymphocytes. Red and green fluorescence were measured and compared to non-specific control FITC- and biotin- conjugated monoclonal antibodies. Cells unreactive with either monoclonal antibody were non T cells (lower left corner); cells that were double positive, i.e. reacting with both OKT®3 and βF1, make up the large population of lymphocytes in the center region of the grid; cells that were βF1− but OKT®3+ comprise a small but distinct group of lymphocytes (4% of the T3+ cells) observed along the X-axis.

A. IDP1 cell line 2 (WT31+) and cell line 3 (WT31−). Lanes 1, 2, 7, 8: Normal mouse serum. Lanes 3, 4, 9, 10: Anti-T3 monoclonal antibody (UCHT-1). Lanes 5, 6, 11, 12: Anti-framework TCR α,β monoclonal antibody (βF1).

B. IDP2 cell line 7 (88% WT31−T3+) Lanes 1, 4, 7, 10: Normal mouse serum. Lanes 2, 5, 8, 11: Anti-framework TCR monoclonal antibody (βF1). Lanes 3, 6, 9, 12: Anti-T3 monoclonal antibody (UCHT-1). $^{125}$I-labeled samples XL-cross-linked with DSP.

C. IDP2 cell line 5 (WT31+ T3+) and cell line 7 (88% WT31−T3+). Lanes 1, 3: Normal mouse serum. Lanes 2, 4: Anti-T3 monoclonal antibody (UCHT-1).

A. Lane 1: IDP2 cell line 6 (WT31−). Lane 2: T leukemic cell line HBP-MLT.

B. Lane 1: IDP2 cell line 5 (WT31+T3+). Lane 2: IDP2 cell line 7 (88% WT31−T3+). Lane 3: Cell line HPB-MLT.

A. Lane 1: Normal mouse serum. Lane 2: Anti-V γ peptide mouse serum. Lane 3: Normal rabbit serum. Lane 4: Anti-C γ peptide rabbit serum.

B. Lane 1: Normal mouse serum. Lane 2: Anti-T3 monoclonal antibody (UCHT-1). Lane 3: Normal rabbit serum. Lane 4, 5: Anti-C γ peptide rabbit serum.

DETAILED DESCRIPTION OF THE INVENTION

The present invention provides a purified polypeptide which comprises at least a portion of a δT cell receptor polypeptide. This polypeptide may comprise a δT cell receptor polypeptide having a molecular weight of about 40,000 daltons. Additionally, the δT cell receptor polypeptide may be a human δT cell receptor polypeptide.

A substance capable of specifically forming a complex with at least one δT cell receptor polypeptide is also provided by the invention. In one embodiment of the invention, the substance is capable of specifically forming a complex with one δT cell receptor polypeptide. In another embodiment of the invention, the substance is capable of specifically forming a complex with more than one δT cell receptor polypeptide. The substance may be an antibody. The antibody may be a polyclonal antibody or a monoclonal antibody.

Also provided is a method for detecting T cells, each of which has a δT cell receptor polypeptide. This method comprises contacting a sample containing T cells with substances capable of forming complexes with δT cell receptor polypeptides so as to form cellular complexes between the substances and the δT cell receptor polypeptides. These cellular complexes are detected and thereby T cells, each of which has a δT cell receptor polypeptide, are detected.

Within this application, cellular complexes means complexes formed within T cells or on the surface of T cells. However, non-cellular complexes may be formed with polypeptides provided by the present invention which are soluble, i.e. cell-free. These soluble polypeptides may be detected, quantified and compared with other markers for diagnosing immune system abnormalities in a subject. Accordingly, in one embodiment of the invention, the δT cell receptor polypeptides are present on the surfaces on the T. cells. In another embodiment of the invention, the δT cell receptor polypeptides are present in the cytoplasm of the T cells.

This method may be performed by forming complexes with a specific δT cell receptor polypeptide. In one embodiment of the invention, the specific δT cell receptor polypeptide is present only in suppressor T cells.

The invention further provides a method for diagnosing an immune system abnormality in a subject. Within this application, immune system abnormality means a condition of immunological responsiveness to antigens characterized by an increased or a decreased immune response compared to a normal or standard immune response. Accordingly, immune system abnormality includes, but is not limited to, immunodeficiency conditions and diseases, e.g. acquired immune deficiency syndrome and congenital immunodeficiencies and, hyperimmune conditions and diseases, e.g. allergies and hayfever. The method of the present invention comprises determining the number of T cells in a sample from the subject and contacting the sample with the substances capable of forming complexes with at least one δT cell receptor polypeptide so as to form cellular complexes between the substances and δT cell receptor polypeptides. The percentage of T cells in the sample which have a δT cell receptor polypeptide is determined and compared with the percentage of T cells which have a δT cell receptor polypeptide in a sample from a normal subject who does not have the immune system abnormality. A difference in the percentage of T cells so determined would be indicative of the immune system abnormality.

In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In still a further embodiment of the invention, the immune system abnormality is an autoimmune disease.

The subject in whom the immune system abnormality is diagnosed may be an animal. In one embodiment of the invention the subject is a human. Furthermore, the sample from the subject may comprise blood or tissue. However, methods of diagnosing immune system abnormalities may be performed by forming non-cellular complexes with soluble polypeptides in samples derived from blood, tissue, plasma, serum or urine.

Yet another method for diagnosing an immune system abnormality is provided by the present invention. This method comprises determining the number of δT cell receptor polypeptide bearing T cells in a sample from the subject and the amount of δT cell receptor polypeptides in the T cell receptor polypeptide bearing T cells. The amount of δT cell receptor polypeptides so determined is compared with the amount of δT cell receptor polypeptides in an equal number of δT cell receptor polypeptide bearing T cells in a sample from a normal subject who does not have the immune system abnormality. A difference in the amount so determined would be indicative of the immune system abnormality. In one embodiment of the invention, the amount of a single δT cell receptor polypeptide is determined.

A further method for diagnosing an immune system abnormality in a subject is provided. This method comprises determining in a sample from the subject the number of T cells which have a δT cell receptor polypeptide and the number of T cells consisting of the group of T cells which have one of the surface markers T4, T8 and α, β a T cell receptor. The numbers of T cells so determined is compared with the number of T cells which have a δT cell receptor polypeptide and the number of T cells in the group which have the same surface marker as the group of T cells determined in the sample from the subject, in a sample from a subject who does not have the immune system abnormality. A difference in the number of T cells so determined which have a δT cell receptor polypeptide relative to the number of T cells in the group so determined would be indicative of the immune system abnormality.

The present invention also provides a nucleic acid molecule encoding a δT cell receptor polypeptide having a molecular weight of about 40,000 daltons. In one embodiment of the invention, the molecule is a DNA molecule. Further provided is a nucleic acid molecule which is complementary to the nucleic acid molecule which encodes a δT cell receptor polypeptide.

A purified polypeptide which comprises at least a portion of a γT cell receptor polypeptide is also provided by the present invention. This polypeptide may comprise a γT cell receptor polypeptide having a molecular weight of about 55,000 daltons. Additionally, the polypeptide may be a human γT cell receptor polypeptide.

The present invention also provides a substance capable of specifically forming a complex with at least one γT cell receptor polypeptide. In one embodiment of the invention, the substance is capable of specifically forming a complex with one γT cell receptor polypeptide. In another embodiment of the invention, the substance is capable of specifically forming a complex with more than one γT cell receptor polypeptide. The substance may be an antibody. In one embodiment of the invention, the antibody is a polyclonal antibody. In another embodiment of the invention, the antibody is a monoclonal antibody.

A method for detecting T cells, each of which has a γT cell receptor polypeptide, is further provided. This method comprises contacting a sample which contains T cells with substances capable of forming complexes with γT cell receptor polypeptides so as to form cellular complexes between the substances and the γT cell receptor polypeptides. These cellular complexes are detected and thereby T cells, each of which has a γT cell receptor polypeptide, are detected. In one embodiment of the invention, the γT cell receptor polypeptides are present on the surfaces of the T cells. In another embodiment of the invention, the γT cell receptor polypeptides are present in the cytoplasm of the T cells. In yet another embodiment of the invention, the substances are capable of forming complexes with a specific γT cell polypeptide. The specific γT cell receptor polypeptide may be present only in suppressor T cells.

The present invention further provides a method for diagnosing an immune system abnormality in a subject. This method comprises determining the number of T cells in a sample from the subject and contacting the sample with substances capable of forming complexes with at least one γT cell receptor polypeptide so as to form cellular complexes between the substances and γT cell receptor polypeptides. The percentage of T cells in the sample which have a γT cell receptor polypeptide is determined and compared with the percentage of T cells which have a γT cell receptor polypeptide in a normal subject who does not have the immune system abnormality. A difference in the percentage of T cells so determined would be indicative of the immune system abnormality. In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In still a further embodiment of the invention, the immune system abnormality is an autoimmune disease.

The subject in which the immune system abnormality is diagnosed may be an animal. Additionally, the subject in which the immune system abnormality is diagnosed may be a human. Furthermore, the sample of which the percentage of T cells which have a γT cell receptor polypeptide is determined may comprise blood or tissue.

Yet another method for diagnosing an immune system abnormality in a subject is provided by the present invention. This method comprises determining the number of γT cell receptor polypeptide bearing T cells in a sample from the subject and the amount of γT cell receptor polypeptides in the γT cell receptor polypeptide bearing T cells. The amount of γT cell receptor polypeptides so determined is compared with the amount of γT cell receptor polypeptides in an equal number of γT cell receptor polypeptide bearing T cells in a sample from a normal subject who does not have the immune system abnormality. A difference in the amount so determined would be indicative of the immune system abnormality. In one embodiment of the invention, the amount of a single γT cell receptor polypeptide is determined.

Further provided is another method for diagnosing an immune system abnormality in a subject. This method comprises determining in a sample from the subject the number of T cells which have a γT cell receptor polypeptide and the number of T cells consisting of the group of T cells which have one of the surface markers T4, T8 and α,β T cell receptor. The numbers of T cells so determined are compared with the number of T cells which have a γT cell receptor polypeptide and the number of T cells in the group which have the same surface marker as the group determined in the sample from the subject, in a sample from a subject who does not have the immune system abnormality. A difference in the number of T cells so determined which have a γT cell receptor polypeptide relative to the number of T cells in the group so determined would be indicative of the immune system abnormality.

A purified complex which comprises at least a portion of a $\delta$T cell receptor polypeptide and at least a portion of a $\gamma$T cell receptor polypeptide is further provided by the present invention. This complex may comprise a $\delta$T cell receptor polypeptide having a molecular weight of about 40,000 daltons and a $\gamma$T cell receptor polypeptide having a molecular weight of about 55,000 daltons. Furthermore, the $\delta$T cell receptor polypeptide may be a human $\delta$T cell receptor polypeptide and the $\gamma$T cell receptor polypeptide may be a human $\gamma$T cell receptor polypeptide.

Also provided is a substance capable of specifically forming a complex with at least one $\gamma$, $\delta$T cell receptor complex. This substance may be capable of forming a complex with one $\gamma$,$\delta$T cell receptor complex. Furthermore, the substance may be capable of forming a complex with more than one $\gamma$,$\delta$T cell receptor complex.

In one embodiment of the invention, the substance is an antibody. In another embodiment of the invention, the substance is a polyclonal antibody. In yet another embodiment of the invention, the substance is a monoclonal antibody.

The present invention further provides a method for detecting T cells, each of which has a $\gamma$,$\delta$T cell receptor complex. This method comprises contacting a sample containing T cells with substances capable of forming complexes with $\gamma$,$\delta$T cell receptor complexes so as to form cellular complexes between the substances and the $\gamma$,$\delta$T cell receptor complexes. These cellular complexes are detected and thereby T cells, each of which has a $\gamma$, $\delta$T cell receptor complex, are detected. In one embodiment of the invention, the $\gamma$,$\delta$T cell receptor complexes are present on the surface of the T cells. In another embodiment of the invention, the $\gamma$, $\delta$T cell receptor complexes are present in the cytoplasm of the T cells. In yet another embodiment of the invention, the substances are capable of forming complexes with a specific $\gamma$,$\delta$T cell receptor complex. The specific $\gamma$, $\delta$T cell receptor complex may be present only in suppressor T cells.

A method for diagnosing an immune system abnormality in a subject is further provided by the present invention. This method comprises determining the number of T cells in a sample from the subject and contacting the sample with substances capable of forming complexes with at least one $\gamma$, $\delta$T cell receptor complex so as to form cellular complexes between the substances and $\gamma$,$\delta$T cell receptor complexes. The percentage of T cells in the sample which have a $\gamma$,$\delta$T cell receptor complex is determined and compared with the percentage of T cells which have a $\gamma$, $\delta$T cell receptor complex in a sample from a normal subject who does not have the immune system abnormality. A difference in the percentage of T cells so determined would be indicative of the immune system abnormality. In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In yet a further embodiment of the invention, the immune system abnormality is an autoimmune disease.

The subject in which the immune system abnormality is diagnosed may be an animal. Furthermore, the subject in which the immune system abnormality is diagnosed may be a human. Moreover, the sample in which the percentage of T cells which have a $\gamma$, $\delta$T cell receptor complex is determined may comprise blood or tissue.

Still another method for diagnosing an immune system abnormality in a subject is provided by the present invention. This method comprises determining the number of $\gamma$, $\delta$T cell receptor complex bearing T cells in a sample from the subject and the amount of $\gamma$,$\delta$T cell receptor complexes in the $\gamma$, $\delta$T cell receptor complex bearing T cells. The amount so determined is compared with the amount of $\gamma$, $\delta$T cell receptor complexes in an equal number of $\gamma$, $\delta$T cell receptor complex bearing T cells in a sample from a normal subject who does not have immune system abnormality. A difference in the amount so determined would be indicative of the immune system abnormality. In one embodiment of the invention, the amount of a single $\gamma$, $\delta$T cell receptor complex is determined.

Yet a further method for diagnosing an immune system abnormality is provided. This method comprises determining in a sample from the subject the number of T cells which have a $\gamma$, $\delta$T cell receptor complex and the number of T cells consisting of the group of T cells which have one of the surface markers T4, T8 and $\alpha$,$\beta$ T cell receptor complex. The numbers of T cells so determined are compared with the number of T cells which have a $\gamma$, $\delta$T cell receptor and the number of T cells in the group which have the same surface marker as the group of T cells determined in the sample from the subject, in a sample from a subject who does not have the immune system abnormality. A difference in the number of T cells so determined which have a $\gamma$, $\delta$T cell receptor complex relative to the number of T cells in the group so determined would be indicative of the immune system abnormality.

Furthermore, the polypeptides and the substances provided by the present invention may be used as therapeutic agents for the treatment of immune system abnormalities. Moreover, the substances provided by the present invention, e.g., monoclonal antibodies capable of specifically forming complexes with at least a portion of a $\gamma$, a $\delta$ or a $\gamma$,$\delta$T cell receptor polypeptide, may be useful as reagents for the in vivo diagnosis, e.g. imaging, of immune system abnormalities.

The various methods for diagnosing abnormalities and for detecting T cells provided by the present invention are based upon the novel polypeptides and substances capable of forming complexes with these polypeptides as described more fully hereinabove. The methods utilize methods for detecting and quantifying T cells, including but not limited to, fluorescence activated cell sorting and autoradiography, which are well known to those skilled in the art to which this invention pertains.

Materials and Methods

Lymphocyte Culture and Cell Population Analysis

Viable lymphocytes were isolated by ficoll-hypaque density centrifugation and stained with 0.5 micrograins of a specific monoclonal antibody, e.g. WT31 (28, 29) or OKT®3, OKT®4 or OKT®8 (Ortho Diagnostic Systems, Inc., Raritan, N.J.), for 30 minutes at 4° C. After washing, the cell pellets were stained again with fluorescein isothiocyanate (FITC)-conjugated goat anti-mouse IgF(ab)'$_2$ fragments. Fluorescence activated cell sorter(FACS) analyses were performed on an Ortho cytofluorograph or a Coulter Epics as previously described (37). Specifically stained positive cells were determined relative to a negative control profile for each cell line (stained with a nonspecific control monoclonal antibody). Cells having fluorescence intensity channel numbers greater than the intercept of the negative control profile with the baseline were counted as positive, and the % positive was calculated relative to the total number of cells counted.

All cell lines were propagated in vitro in media composed of RPMI 1640, 10% human serum and conditioned media containing 2-5 units of interleukin-2 activity as previously described (34).

Alloantigen (allo) activated cultures were stimulated with irradiated allogenic peripheral blood lymphocytes at weekly intervals. Mitogen, i.e. phytohemagglutinin (PHA), activated lines were stimulated with a 1:1,000 dilution of PHA (Difco, Detroit, Mich.) at culture initiation.

Reactivity and Characterization of Cell Culture Using Monoclonal Antibodies

Immunoprecipitates from $^{125}$I-labeled lymphocyte lysates were analyzed by sodium dodecyl sulfate-polyacrylamide gel electrophoresis (SDS-PAGE). The radioiodinated T leukemia cell lines HPB-MLT and Jurkat, the HTLV-1 transformed cell line ANITA and resting peripheral blood lymphocytes were solubilized in 1% Triton-X-100 (TX-100) and immunoprecipitated with a control antibody, normal mouse serum (NNS) or a framework antibody to TCR $\alpha$, $\beta$ i.e. , $\beta$Fl (54). The $\beta$Fl monoclonal antibody was prepared according to standard procedures (47, 52). Spleen cells from mice immunized with purified TCR $\alpha,\beta$ as described in (28) were used for the fusion experiments. A positive clone, $\beta$Fl, was obtained by immunoprecipitation with T cell lines and peripheral blood lymphocytes as described above.

$^{125}$I-labeled lymphocytes were solubilized in 0.1% TX-100 and immunoprecipitated with NMS, the anti-T3 anti-body UCHT-1 (40) and a framework antibody to TCR i.e., WT31. The efficiency of immunoprecipitation with WT31 was improved at the lower TX-100 concentration used here and the monoclonal antibody 187.1 (53) was used as a second antibody.

Two-color FACS analysis of normal adult peripheral blood lymphocytes was performed using an anti-TCR $\alpha,\beta$ monoclonal antibody and an anti-T3 monoclonal antibody. Peripheral blood lymphocytes were stained first with an FITC-conjugated anti-T3 monoclonal antibody (OKT®3) and then with a biotinyl-anti-TCR $\alpha,\beta$ monoclonal antibody ($\beta$Fl) followed by phycoerythrin-conjugated avidin (PE-avidin, Becton Dickinson, Mt. View, Calif.).

Viable lymphocytes were isolated by ficoll-hypaque density centrifugation for SDS-PAGE and FACS analyses. For SDS-PAGE analysis, lymphocytes were radioiodinated by the lactoperoxidase technique, solubilized in 1% TX-100 and immunoprecipitated using 1 microgram of a specific antibody, i.e. monoclonal antibody $\beta$Fl or monoclonal antibody UCHT-1, or 1 microliter of NMS. The immunoprecipitates were then analysed by 10.5% SDS-PAGE under reducing conditions. The $^{125}$I-labeled molecules were visualized by autoradiography as previously described (28).

Two-colored cytofluorographic analysis was performed by first staining with FITC-OKT®3 monoclonal antibody for 45 minutes at 40° C. After washing, the lymphocytes were fixed in 1% paraformaldehyde for 15 minutes at 23° C. then incubated in 70% ethanol in phosphate buffered saline (PBS) for 5 minutes at −20° C. After further washing, the cells were stained with the biotinyl-$\beta$Fl monoclonal antibody followed by PE-avidin. Analysis was performed on an Ortho® cytofluorograph (Ortho Diagnostic Systems, Inc., Westwood, Mass.).

Analysis of Cell Surface Protein Molecules Associated with T3 Molecules on IDP1 and IDP2 Cell Lines IDP1 cell line 2 (WT31+) and cell line 3 (WT31−) were $^{125}$I-labeled as described above. Radioiodinated, intact lymphocytes were then either cross-linked by incubation in PBS (pH 8) containing 50 micrograms/ml dithio-bis-succinimidyl propionate (DSP) or mock incubated. The cells were then solubilized in 1% TX-100 and immunoprecipitated as previously described (12). T3 associated molecules ($M_r$ 40,000-55,000) in the anti-T3 immunoprecipitations were detected at low levels in the noncross-linked samples and at higher levels in the cross-linked samples.

IDP2 cell line 7 (88% WT31−T3+) was $^{125}$I-labeled and treated with DSP or mock incubated. Immunoprecipitations were performed using NMS, the anti-T3 monoclonal antibody UCHT-1 and the anti-TCR $\alpha$, $\beta$ monoclonal antibody $\beta$Fl either without or with preclearing TCR $\alpha,\beta$ molecules with the monoclonal antibody $\beta$Fl. A small fraction of radiolabeled TCR $\alpha,\beta$ was detected in samples which were not precleared but not in samples which were precleared with $\beta$Fl.

IDP2 cell line 5 (WT31+T3+) and cell line 7 (88% WT31−T3+) were $^{125}$I-labeled, solubilized in 1% TX-100 and immunoprecipitated using NMS or the anti-T3 monoclonal antibody UCHT-1. The T3 heavy subunit ($M_r$ 27,000) appeared similar on these two cell lines, while the T3 light subunits ($M_r$ 19,000-25,000) did not.

$^{125}$I-labeling, solubilization in 1% TX-100, immunoprecipitation and visualization after 10.5% SDS-PAGE analysis by autoradiography were perfomed as previously described (28). Chemical cross-linking was perfomed for 30 minutes at 23° C. on intact radiolabeled lymphocytes using DSP (50 micrograins/ml) in PBS (pH 8) as previously described (12). After immunoprecipitation, all samples were examined by SDS-PAGE under reducing conditions using 5% 2-mercaptoethanol, which cleaved both the disulfide bonds between protein subunits and the DSP chemical cross-link.

Northern Blot Analysis of RNA Isolated from IDP2 Cell Lines Using TCR $\alpha$, TCR $\beta$ and TCR $\gamma$ cDNA Probes Total RNA (15 micrograins) isolated from IDP2 cell line 6 (WT31−) and from T leukemic cell line HBP-MLT was fractionated on a 1.5% agarose gel containing 2.2M formaldehyde, transferred to nitrocellulose and hybridized with TCR $\alpha$, TCR $\beta$ and TCR $\gamma$ probes.

Total RNA (3 micrograins) isolated from IDP2 cell line 5 (WT31+T3+), IDP2 cell line 7 (88% WT31−T3+) and HPB-MLT was analyzed as described above.

RNA preparation, electrophoresis, transfer to nitrocellulose and hybridization with $^{32}$P-labeled, nick-translated probes (1-3×10$^8$ cpm/microgram) were as described previously (41). $\alpha$-chain probes were either the human cDNA clones pGA5(8) or L17$\alpha$ (42). $\beta$ chain probes were either the human cDNA clones 12A1 (43) or L17β (43). The γ-chain probe was an EcoRI to AccI fragment derived from human cDNA clone Tγ-1 (36). Radioactive bands were visualized by autoradiography using intensifying screens. All probes were labeled to nearly identical specific activity, and identical exposure times are presented.

Immunoprecipitation of IDP2 Cell Line 7 Surface Molecules Using anti-γ Antiserum TX-100 solubilized $^{125}$I-labeled IDP2 cell line 7 (88% WT31−T3+) was denatured (see below) and then immunoprecipitated with NMS or normal rabbit serum and with anti-V γ peptide serum or anti-C γ peptide serum. A specific band was observed at $M_r$ 55,000 in both the anti-V γ and anti-C γ immunoprecipitations. The additional band at $M_r$ 90,000 was not reproducibly observed in the anti-C γ immunoprecipitations (see below).

DSP cross-linked native lysates (1% TX-100) from $^{125}$I-labeled IDP2 cell line 7 were immunoprecipitated with NMS or with the anti-T3 monoclonal antibody UCHT-1. Alternatively, the lysate was denatured (as described below) and immunoprecipitated with either normal rabbit serum or with anti-C γ peptide serum.

An additional aliquot of lysate was subjected to a two stage immunoprecipitation. Polypeptides were immunoprecipitated with the anti-T3 monoclonal antibody UCHT-1, and were eluted from the immunoabsorbent under denaturing and reducing conditions, in order to break the DSP cross-link. Immunoprecipitation from this eluate was then performed using anti-C γ peptide serum.

$^{125}$I-labeling, solubilization in 1% TX-100 and immuno-precipitation were performed as described above. Native lysates (1% TX-100) were denatured by the addition of SDS (final concentration of 1%) and dithiothreitol (final concentration of 2 mm) followed by heating the mixture for 5 minutes at 68° C. After cooling, iodoacetamide was added (20 mM final concentration) and samples were diluted with the addition of 4 volumes of 1.5% TX-100 in Tris buffered saline (pH 8). The initial immunoprecipitate in the experiment was denatured and subsequently partially renatured (28). Samples were immunoprecipitated with 10 microliters of anti-C γ or anti-V γ peptide sera, 1 microgram of UCHT-1 or 1 microliter of NMS or normal rabbit serum and analyzed by 10.5% SDS-PAGE under reducing conditions (5% 2-mercaptoethanol).

Peptides corresponding to deduced V γ or C γ amino acid sequences (residue numbers noted below in the Experimental Result section) were synthesized on a Beckman 990 peptide synthesizer using the method of Erickson and Merrifield (44). Peptide purity was assessed by high pressure liquid chromatography and peptide sequence was confirmed by amino acid analysis. Peptides were coupled to keyhole limpet hemocyanin (KLH) at a ratio of 50 peptides per KLH molecule (45). Mice and rabbits were immunized with the V γ peptides or C γ peptides, respectively. Animals were injected at three week intervals and the antisera screened for binding reactivity on peptide-KLH and peptide-bovine serum albumin conjugates to ascertain the presence of peptide-specific antibodies.

Monoclonal antibodies against the γ chain were generated by standard procedures as described in (47, 50). BALB/c mice were immunized with the KLH-coupled peptide to the variable region γ chain peptide described above using the method of Erickson and Merrifield (44). After four immunizations at two week intervals, spleen cells were fusea with P3-X63-Ag8U1 myeloma cells. Positive hybridoma clones were screened and identified by the enzyme immunoassay (EIA) described in (48).

Isolation of DNA Sequences of the δ Polypeptide Using Sequences From Purified Proteins DNA sequences of the TCR δ gene may be isolated and determined by strategies utilized to isolate the TCR β gene as described in (49, 50). Briefly, the amino acid sequence of the TCR δ gene may be determined following isolation of the TCR δ polypeptide which is described hereinafter. After the amino acid sequence is determined, short, synthetic DNA sequences may be prepared using a commercial DNA synthesizer (Applied Biosystems,, Inc., Foster City, Calif.). The synthetic DNA sequences may be used as probes for the isolation of the complete sequence of DNA from a cDNA library of cell lines containing the TCR δ polypeptide. The complete primary structure of the protein may then be determined (51).

Preparation of Monoclonal Antibodies Against the δ Polypeptides and Against γ,δ Complexes Monoclonal antibodies against the δ polypeptide may be generated by standard procedures (47, 50). Peptides derived from the TCR δ polypeptide may be prepared from nucleic acid sequences determined by the methods described above. Methods for the selection of such peptides useful for immunization have been described in detail (55, 56, 57).

Monoclonal antibodies directed against γ,δ complexes may be prepared according to published procedures (47, 50). γ,δ complexes may be isolated from the T cell lines described above and used to immunize BALB/c mice as described in previously published procedures (28). Alternatively, BALB/c mice may be immunized with cell lines, e.g., the IDP1 cell line or the IDP2 cell line.

Methods for the fusion, generation and maintenance of hybridoma cell lines have been widely published and are known to those skilled in the art. Hybridoma cells that produce monoclonal antibodies which are directed against specific TCR γ,δ cell lines but which do not cross react with other T cell lines may be selected and recovered.

Experimental Results

Figure 1A:
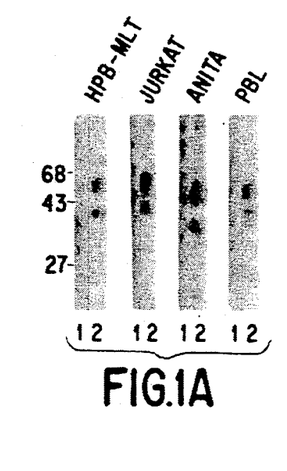
FIGS. 1A-1C: Reactivity of framework monoclonal antibodies recognizing TCR α,β.
Figure 1B:
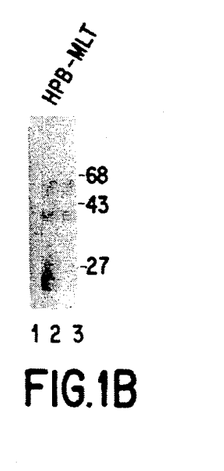
Figure 1C:
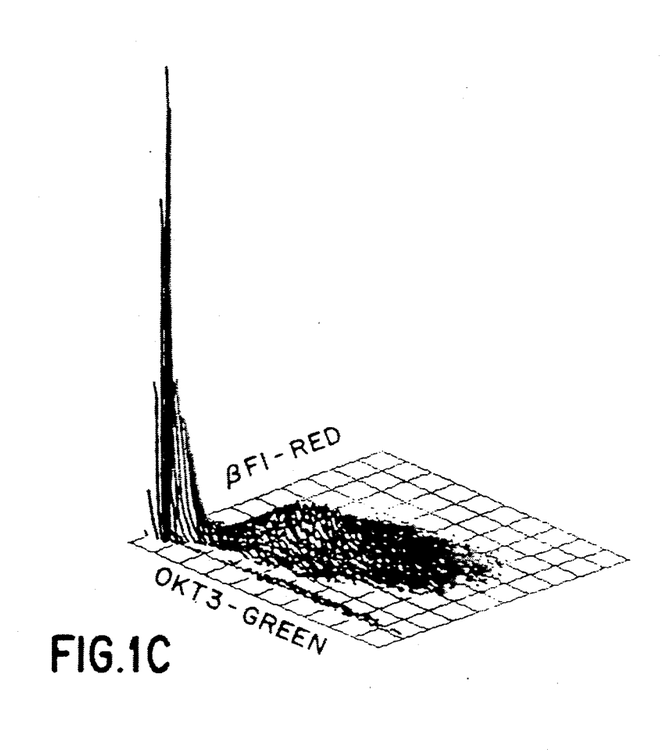

A murine framework antiserum that recognizes the majority of human TCR α, β molecules has previously been reported (28). Subsequently, a murine monoclonal antibody, designated β Framework 1 (βF1) , that is reactive with shared determinants on the human TCR β chain was obtained (46). The βF1 monoclonal antibody reacts with the majority of T3 positive (T3+) human peripheral blood lymphocytes (PBLs) and is capable of immunoprecipitating the TCR α, β heterodimer from all human T cell lines examined that have α, β T cell receptors and express the T3 glycoprotein. Immunoprecipitations from a panel of T cell lines using this monoclonal antibody demonstrate this reactivity as well as the heterogeneity of the TCR α and TCR β subunits from different receptors (FIG. 1A). Like the framework antiserum (28), this monoclonal antibody does not stain the surface of living T cells, but will specifically react with both membrane and cytoplasmic T cell receptors after partial solution of the lymphocyte plasma membrane with 70% ethanol. Double staining of human PBLs with a fluorescein-anti-T3 monoclonal antibody and a biotinyl-βF1 monoclonal antibody followed by PE avidin reveals that the βF1 monoclonal antibody recognizes 95-97% of peripheral blood T3+ lymphocytes. However, it clearly defines a small population of T lymphocytes that is βF1 negative (βF1−), yet T3+ (FIG. 1C).

A second framework monoclonal antibody designated WT31, initially thought to recognize the T3 antigen (29), has recently been shown to react with a common epitope of human TCR α,β (30). While double staining with an anti-T3 monoclonal antibody (OKT3) and WT31 revealed that each of these monoclonal antibodies cross-block binding of the other, one-color fluorescence indicated that WT31 typically recognized 1-3% fewer cells in peripheral blood than do anti-T3 monoclonal antibodies. The WT31 monoclonal antibody efficiently binds to the surface of T cells (such as in FACS analyses) and is capable of immunoprecipitating the TCR α, β molecules, albeit inefficiently, from radiolabeled detergent lysates (30) (FIG. 1B lane 3). Thus, the βF1 monoclonal antibody and the WT31 monoclonal antibody appear to recognize all but a small fraction of human peripheral blood T3+ cells, and define a subpopulation that is T3+ but unreactive with both of these framework monoclonal antibodies against the TCR α, β molecules. Evidence that the T3+ lymphocytes that are unreactive with the monoclonal antibody βF1 are also unreactive with the monoclonal antibody WT31 is shown below. WT31 was used primarily for FACS analyses and βF1 was used primarily for immunoprecipitation studies.

Efforts at growing the WT31−T3+ population from normal adult PBLs proved difficult, since the WT31+T3+ lymphocytes usually overgrew the WT31−T3+ cells following mitogenic stimulation. However, growth of the WT31−T3+ population from the PBLs of immunodeficiency patients was successful. Immunodeficiency patient 1 (IDP1) suffered from the bare lymphocyte syndrome and lacked class II MHC antigen expression on lymphoid cells (31, 32), while immunodeficiency patient 2 (IDP2) suffered from an ectodermal dysplasia syndrome (33) and displayed poor in vitro T cell proliferative responses to mitogens.

After activation of PBLs from IDP1 with alloantigen and propagation in conditioned media containing interleukin-2 (IL-2) activity (34), the resultant cell line was observed to be approximately. 50% WT31+T3+ and 50% WT31−T3+ (see Table I below, cell line 1). Subsequent sorting of this cell line yielded homogeneous populations of WT31+T3+ cells and WT31−T3+ cells (see Table I below, cell lines 2 and 3, respectively).

TABLE 1

| CELL LINE NUMBER | SOURCE | CELL LINE[1] DESCRIPTION | % POSITIVE | | | |
|---|---|---|---|---|---|---|
| | | | WT31 | T3 | T4 | T8 |
| 1 | IDP1 | allo | 50 | 100 | 11 | 50 |
| 2 | IDP1 | WT31+ sort | 100 | 100 | 70 | 28 |
| 3 | IDP1 | WT31− sort | 0 | 100 | 0 | 62 |
| 4 | IDP2 | fresh PBL | 61 | 63 | 38 | 16 |
| 5 | IDP2 | PHA | 100 | 96 | 18 | 80 |
| 6 | IDP2 | allo | 2 | 100 | 0 | 43 |
| 7 | IDP2 | PHA | 12 | 93 | 1 | 18 |

[1]Cell line description indicates the conditions for activation or source of lymphocytes. W31+ and WT31− sorted cell lines 2 and 3 (sort) were obtained by flourescence activated cell sorting of IDP1 cell line 1.

Cell lines were also obtained from IDP2. Fresh PBLs from IDP2 revealed that 63% of the PBLs were T3+ and 1-3% fewer cells (61%) were WT31+, which is typical of normal PBLs (Table I, cell line 4). Activation of these IDP2 PBLs with either phytohemagglutinin (PHA) or alloantigen and propagation in vitro with conditioned media resulted in several cell lines. These included a homogeneous WT31+T3+ cell line (Table I, cell line 5), a homogeneous WT31−T3+ cell line (Table I, cell line 6) and on a third occasion, a cell line that was 88% WT31−T3+ (with 12% contaminating WT31+T3+ cells) (Table I, cell line 7). The WT31−T3+ population contained both T4−T8+ and T4−T8− cells (Table I, cell lines 3, 6 and 7). Further phenotypic analysis revealed that this population was T11+ but negative for natural killer cell markers such as Leu 7, Leu 11 and OKM1 and for the immature thymocyte marker T6.

Figure 2A:
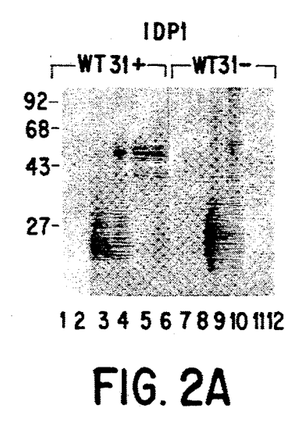
FIGS. 2A–2C: SDS-PAGE analysis of cell surface T3 and T3-associated (cross-linked) molecules by immunoprecipitation from IDP1 and IDP2 cell lines.
Figure 2B:
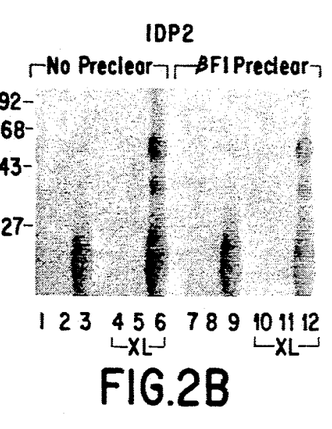
Figure 2C:
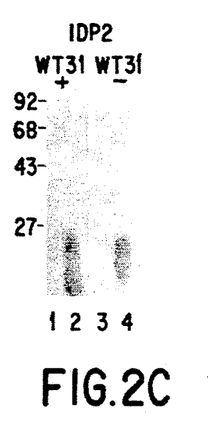

The βF1 monoclonal antibody immunochemically defined a heterodimeric structure on the surface of $^{125}$I-labeled WT31+T3+ IDP1 lymphocytes (FIG. 2A, lane 5), yet failed to recognize a similar protein on the WT31−T3+ population from this same individual (FIG. 2A, lane 11). Similar analysis of IDP2 cell lines revealed a trace of TCR α, β on the 88% WT31−T3+ cell line 7 (FIG. 2B, lane 2) consistent with the 12% contamination with the WT31+T3+ cells. Thus, the WT31−T3+ cells, identified by the lack of cell surface reactivity with the WT31 monoclonal antibody in FACS analysis, were also βF1−, as determined by the lack of TCR α, β on immunoprecipitation. All WT31+T3+ and WT31−T3+ cell lines expressed similar amounts of T3 by FACS analysis and by immunoprecipitation with an anti-T3 monoclonal antibody (FIG. 2A, lanes 3 and 9; FIG. 2C, lanes 2 and 4). However, the T3 molecule found on WT31−βF1−T3+ lymphocytes was not identical to the T3 molecule found on WT31+βF1+T3+ cells by SDS-PAGE. One-dimensional (FIG. 2C) and two-dimensional gel analysis indicated that the difference in T3 was restricted to the light T3 subunits, which reproducibly displayed different SDS-PAGE mobilities (FIG. 2C, arrowhead).

Figure 3A:
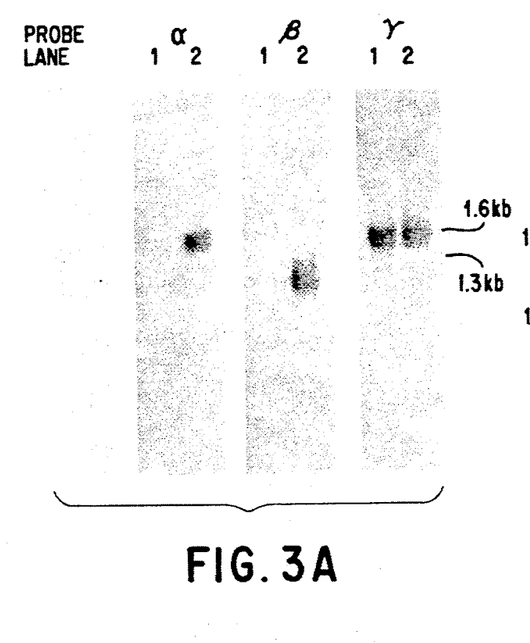
FIGS. 3A–3B: Northern blot analysis of RNA isolated from IDP2 cell lines using TCR α, TCR β and TCR γ cDNA probes.
Figure 3B:
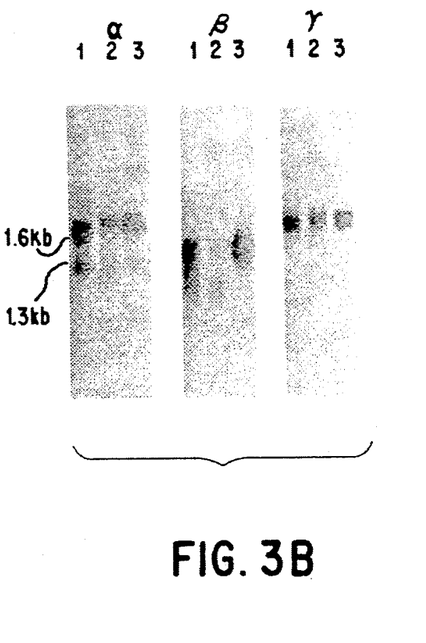

To determine if the WT31−βF1−T3+ population lacked TCR α,β molecules, or alternatively expressed TCR α, β molecules that failed to react with these monoclonal antibodies, the presence of mRNAs encoding the TCR α and β proteins was investigated. $^{32}$P-labeled cDNA clones encoding TCR α, TCR β and TCR γ were used to probe Northern blots containing whole cell RNA from WT31−βF1−T3+ and WT31+βF1+T3+ IDP2 cell lines and from HPB-MLT, which is known to contain mRNA for TCR α, TCR β and TCR γ. No TCR α or TCR β mRNA transcripts could be detected in the RNA from the WT31−βF1−T3+ IDP2 cell line 6 (FIG. 3A α-probe, lane 1; or β-probe, lane 1), whereas expression of both was clearly detectable in RNA from HPB-MLT (FIG. 3A α-probe, lane 2; and β-probe, lane 2). Notably, TCR γmRNA was present in the WT31−T3+ cells at levels comparable to that in HPB-MLT (FIG. 3A γ-probe, lanes 1 and 2). Thus, the WT31−βF1−T3+ lymphocytes lacked TCR α and β mRNA. Subsequent experiments on cell lines that were mostly WT31−T3+ corroborated these results. For example, Northern blot analysis performed on IDP2 cell line 7 (88% WT31−T3+) and compared with IDP2 cell line 5 (WT31+T3+), as well as with HPB-MLT cells, revealed only a trace of TCR α or TCR βmRNA in the 88% WT31−T3+ cells (consistent with the 12% contamination with WT31+T3+ cells) (FIG. 3B, lane 2 for each probe). Further, the majority of the β transcripts that could be detected were 1.0 and not 1.3 kb and were probably nonfunctional (35). In contrast, the IDP2 cell line 5 (WT31+T3+) expressed levels of both RNA species which were comparable to HPB-MLT (FIG. 3B, lane 1 for each probe). However, like the WT31−T3+ cell line shown in FIG. 3A, both the WT31−T3+ and the WT31+T3+ cell lines showed TCR γ RNA levels comparable to HPB-MLT (FIG. 3B γ-probe). Thus, the WT31−T3+ cells lacked α and β T cell receptor mRNA (Northern analysis) and α and β T cell receptor proteins (immuno-precipitation and FACS analysis). The presence of TCR γ mRNA in WT31−T3+ cells, while consistent with TCR γ protein expression, could not be taken as strong evidence for this, since many human cell lines that express TCR γ mRNA of normal size may express full length transcripts that are out of frame due to defective V-J joining (36).

To determine if proteins analogous to the TCR α, β molecules existed on the WT31−βF1−T3+ cells, the technique of chemical cross-linking was utilized. This procedure has been used to show directly the physical association of the TCR α, β molecules with the T3 glycoprotein (12). The bifunctional, cleavable reagent, dithio-bis-succinimidyl propionate (DSP) was employed to cross-link $^{125}$I-labeled surface proteins of viable T lymphocytes. After cross-linking, the lymphocytes were solubilized in a non-ionic detergent and immunoprecipitated with an anti-T3 monoclonal antibody. As expected, the WT31+βF1+T3+ lymphocytes revealed that the TCR α and β chains were cross-linked to T3. For example, TCR α, β molecules and T3 were found in anti-T3 or βF1 monoclonal antibody immunoprecipitates from cross-linked IDP1 cell line 2 (WT31+T3+) (FIG. 2A, lanes 4 and 6). However, despite the lack of reactivity with the βF1 monoclonal antibody and lack of TCR α or TCR β mRNA, IDP1 cell line 3 (WT31−T3+) and IDP2 cell line 7 (88% WT31−T3+) both expressed two protein subunits ($M_r$ 55,000 and 40,000) that specifically cross-linked to T3 (FIG. 2A, lane 10; FIG. 2B, lane 6). The mobilities of these T3 associated molecules were clearly different from those of the TCR α and β chains from WT31+T3+ cell lines (compare FIG. 2A, lanes 4 and 10; or FIG. 2B, lanes 5 and 6).

Since IDP2 cell line 7 (88% WT31−T3+) contained 12% WT31+T3+ cells, accounting for the weak βF1 immunoprecipitates noted (FIG. 2B, lane 2), the lysate from these cells was precleared of TCR α,β protein using the βF1 monoclonal antibody. After preclearing, no residual βF1 reactive material could be detected (FIG. 2B, lanes 8 and 11). When this βF1− precleared lysate from cross-linked cells was immunoprecipitated with an anti-T3 monoclonal antibody, $M_r$ 55,000 and 40,000 subunits were still detected (FIG. 2B, lane 12).

Since these WT31−βF1−T3+ cell lines display undetectable levels of TCR α and TCR β mRNA, the molecules found specifically cross-linked to T3 on their cell surfaces cannot represent proteins encoded by the known TCR α or TCR β genes.

cDNA clones representing the rearranging human TCR γ gene would encode a polypeptide with a predicted molecular weight of 40,000 daltons (36). However, unlike the murine TCR γ gene, which does not reveal any N-linked glycoslyation sites (15), the human TCR γ gene reveals five potential sites for N-linked glycosylation, four of which are located in the constant region (36). Since a TCR γ protein has not previously been isolated, it is not known how many of these potential sites may be used. However, a fully glycosylated human TCR γ protein may have a $M_r$ of about 55,000. The heavy chain of the non-α-non-βT3-associated subunits identified on the WT31−βF1−T3+ IDP1 and IDP2 cell lines has a relative mobility on SDS-PAGE of 55,000 daltons (FIG. 2A and 2B).

Figure 4A:
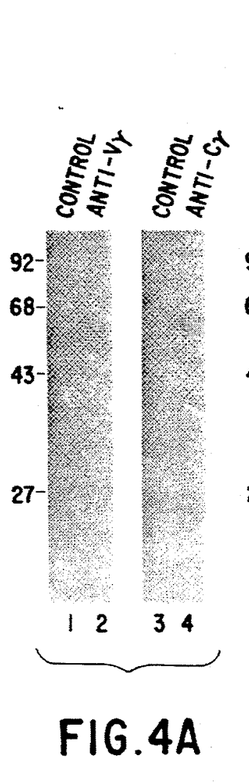
FIGS. 4A and 4B: Anti-V γ and anti-C γ peptide sera immunoprecipitations from IDP2 cell line 7.

In order to determine if this T3-associated heavy chain was serologically cross-reactive with or identical to the TCR γ protein, antisera were raised to a synthetic peptide representing a 17 amino acid stretch of residues (5-21) from the variable region (anti-V γ peptide serum) and to a synthetic peptide representing a 20 amino acid stretch of residues (117-136) from the constant region (anti-C γ peptide serum) of the TCR γ amino acid sequence deduced from a human cDNA clone (35). Both the anti-C γ peptide serum and anti-V γ peptide serum immunoprecipitated a molecule with $M_r$ 55,000 from the denatured lysate of $^{125}$I-labeled WT31−βF1−T3+ cells (FIG. 4A, lanes 2 and 4). Such molecules could not be immunoprecipitated from lysates of $^{125}$I-labeled HPB-MLT cells, which express only nonfunctional TCR γ mRNA (36)

Figure 4B:
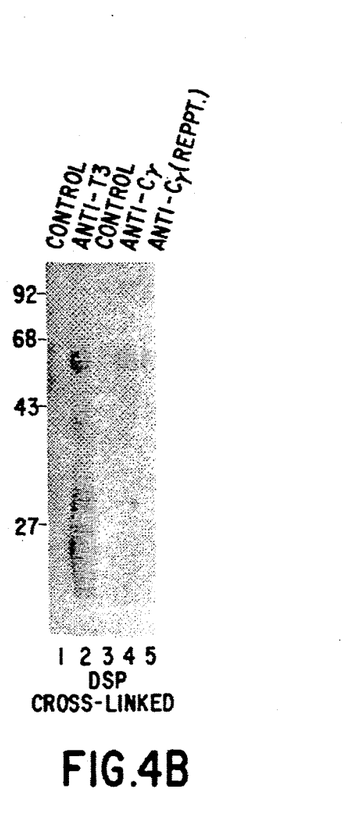

To demonstrate that the 55,000 dalton molecule immunoprecipitated by the anti-C γ and anti-V γ peptide sera was, in fact, the heavy chain subunit that cross-linked to T3, an additional experiment was performed (FIG. 4B). A sample of DSP cross-linked lysate from the WT31−βF1−T3+ cells was first immunoprecipitated with an anti-T3 monoclonal antibody, again demonstrating the presence of $M_r$ 55,000 and 40,000 subunits associated with T3 (FIG. 4B, lane 2). In parallel, another aliquot of the cross-linked lysate was immunoprecipitated with an anti-T3 monoclonal antibody, and the immunoprecipitated T3 cross-linked polypeptides were eluted from the immunoabsorbent under denaturing and reducing conditions in order to break the DSP cross-link. This eluate was then reprecipitated with anti-C γ peptide serum. The $M_r$ 5,000 subunit that cross-linked to T3 was reprecipitated by anti-γ peptide serum (FIG. 4B, lane 5), indicating that the $M_r$ 55,000 subunits defined by these two approaches were identical.

DISCUSSION

Framework monclonal antibodies against the TCR α, β molecules, βF1 and WT31, were used to identify and isolate the WT31−βF1−T3+ lymphocyte population from the peripheral blood lymphocytes of two immunodeficiency patients. By the criteria of both immunoprecipitation analysis with framework monclonal antibodies and Northern blot analysis using TCR α and TCR β specific cDNA probes, polyclonal human T cell lines of this phenotype were shown to express neither TCR α, β mRNA transcripts nor polypeptides. Nevertheless, chemical cross-linking studies using the cleavable DSP reagent revealed the existence of a protein complex associated with the T3 glycoprotein on the surface of these cells. The heavier of the two subunits that cross-linked to T3 ($M_r$ 55,000) was also immunoprecipitated by two different antisera, one generated against a 17 amino acid synthetic peptide corresponding to a part of the variable region and another generated against a 20 amino acid synthetic peptide corresponding to a part of the constant region of the deduced amino acid sequence of a rearranged TCR γ gene (19, 36)

Thus, the $M_r$ 55,000 protein is the TCR γ protein encoded by the rearranging TCR γ gene (15). The $M_r$ 40,000 polypeptide is a fourth T3-associated protein designated TCR δ (FIG. 2A and 2B). The TCR γ and TCR δ polypeptides form a T3-associated heterodimeric structure on these cells (TCRγ, δ-T3) that is analogous to the previously described T cell receptor complex (TCR α, β).

REFERENCE

1. Allison, J. P., McIntyre, B. W. & Bloch, D. J. Immunol. 129, 2293-2300 (1982).
2. Meuer, S. C., Fitzgerald, K. A., Hussey, R. E., Hodgdon, J. C., Schlossman, S. F. & Reinherz, E. L. J.Exp. Med. 157, 705-719 (1983).
3. Haskins, K., Kubo, R., White, J., Pigeon, M., Kappler, J. & Marrack, P. J. Exp. Med. 157, 1149-1169 (1983).
4. Yanagi, Y., Yoshikai, Y., Leggett, K., Clark, S. P., Aleksander, I. & Mak, T. W. Nature 308, 145-149 (1984).
5. Hedrick, S. M., Nielson, E. A., Kavaler, J., Cohen, D. I. & Davis, M. M. Nature 308, 153-158 (1984).
6. Chien, Y., Becker, D. M., Lindsten, T., Okamura, M., Cohen, D. I. & Davis, M. M. Nature 312, 31-35 (1984).
7. Saito, H., Kranz, D. M., Takagaki, Y., Hayday, A. C., Eisen, H. N. & Tonegawa, S. Nature 312, 36-40 (1984).
8. Sim, G. K., Yague, J., Nelson, J., Marrack, P., Palmer, E., Augustin, A. & Kappler, J. Nature 312, 771-775 (1984).
9. Reinherz, E. L., Meuer, S. C., Fitzgerald, K. A., Hussey, R. E., Hodgdon, J. C., Acuto, O. & Schlossman, S. F. Proc. Natl. Acad. Sci U.S.A. 80, 4104-4108 (1983).
10. Oettgen, H. C., Kappler, J., Tax, W. J. M. & Terhorst, C. J. Biol. Chem 259, 12,039-12,048 (1984).
11. Weiss, A. & Stobo, J. D. J. Exp. Med. 160, 1284-1299 (1984).
12. Brenner, M. B., Trowbridge, I. S. & Strominger, J. L. Cell 40, 183-190 (1985).
13. Allison, J. P. & Lanier, L. L. Nature 314, 107-109 (1985).
14. Samelson, L. E. & Schwartz, R. H. Immunol. Rev. 81, 131-144 (1984).
15. Saito, H., Dranz, D. M., Takagaki, Y., Hayday, A. C., Eisen, H. N. & Tonegawa, S. Nature 309, 757-762 (1984).
16. Kranz, D. M., Saito, H., Heller, M., Takagaki, Y., Haas, W., Eisen, H. N. & Tonegawa, S. Nature 313, 752-755 (1985).
17. Hayday, A. C., Saito, H., Gillies, D., Kranz, D. M., Tanigawa, G., Eisen, H. N. & Tonegawa, S. Cell 40, 259-269 (1985).
18. Lefranc, M-P & Rabbitts, T. H. Nature 316, 464-466 (1985).
19. Murre, C. Waldmann, R. A.; Morton, C.C., Bongiovanni, K. F., Waldman, T. A., Shows, T. B. & Seidman, J. G. Nature 316, 549-552 (1985).
20. Quertermous, T., Murre, C., Dialynas, D., Duby, A. D., Strominger, J. L., Waldman, T. A. & Seidman, J. G. Science 231, 252-255 (9186).
21. LeFranc, M-P, Forster, A., Baer, R., Stinson, M. A. & Rabbitts, T. H. Cell 45, 237-246 (1986).
22. Iwamoto, A., Rupp, F., Ohashi, P. S., Walker, C. L., Percher, H., Joho, R., Hengartner, H. & Mak, T. W. J. Exp. Med. 163, 1203-1212 (1986).
23. Zauderer, M., Iwamoto, A. & Mak, T. W. J. Exp. Med. 163, 1314-1318 (1986).
24. Yague, J., White, J., Coleclough, C., Kappler, J., Palmer, E. & Marrack, P. Cell 42, 81-87 (1985).
25. Dembic, Z.,, Haas, W., Weiss, S., McCubrey, J., Keifer, H., von Boehmer, H. & Steinmetz, M. Nature 320, 232-238 (1986).
26. Hedrick, S. M. et al. Proc. Natl. Acad. Sci. U.S.A. 82, 531-535 (1985).
27. Blanckmeister, C. A., Yamamoto, K., Davis, M. M. & Hammerling, G. J. J. Exp. Med. 162, 851-863 (1985).
28. Brenner, M. B., Trowbriage, I. S., McLean, J. & Strominger, J. L. J. Exp. Med. 160, 541-551 (1984).
29. Tax, W. J. M., Willens, H. W., Reekers, P. P. M., Capel, P. J. A. & Koene, R. A. P. Nature 304, 445-447 (1983).
30. Spits, H., Borst, J., Tax, W., Capel. P. J. A., Terhorst, C. & de Vries, J. E. J. Immunol. 135, 1922-1228 (1985).
31. Griscelli, C. Durandy, A., Virelizier, J. L. et al. (1980) In: Seligmann, M. & Hitzig, H. (eds) Primary immunodeficiencies, Elsevier, North-Holland pp 499-503.
32. Hadman, M. R., Dopfer, R. Hans-Harmut, P. & Neithammer, D. (1984) In: Griscelli, C., Vossen, J. (eds) Progress in immunodeficiency research and therapy I. Elsevier Science Publishers B. V., Amsterdam pp 43-50.
33. Levin, L. S., Perrin, J. C. S, Ose, L., Dorst J. P., Miller, J. D. & McKusick, V. A. J. Ped. 90, 55-61 (1977).
34. Brenner, M. B., McLean, J., Yang, S. Y., van der Poel, J. J., Pious, D. & Strominger, J. L. J. Immunol. 135, 384-390 (1985).
35. Yasunobu, Y., Anatoniou, D., Clark, S. P., Yanagi, Y., Sangster, R., Van den Elsen, P., Terhorst, C. & Mak, T. Nature 312, 521-524 (1984).
36. Dialynas, D. P., Murre, C., Quertermous, T., Boss, J. M., Leiden, J. M., Seidman, J. G. & Strominger, J. L. Proc. Natl. Acad. Sci. U.S.A. 83, 2619-2623 (1986).
37. Raulet, D. H., Garman, R. D., Saito, H. & Tonegawa, S. Nature 314, 103-107 (1985).
38. Snodgrass, H. R., Dembic, Z., Steirunetz, M. & von Boehmer, H. Nature 3151 232-233 (1985).
39. De la Hera, A., Toribio, M. L., Marquez, C. & Martinez-A., C. Proc. Natl. Acad. Sci. U.S.A. 82, 6268-6271 (1985).
40. Beverley, P. C. & Collard, R. E. Eur. J. Immunol. 11, 329-334 (1981).
41. Krangel, M. S. EMBO J. 4, 1205-1210 (1985).
42. Leiden, J. M., Fraser, J. D. & Strominger, J. L. In press, Immunogenetics (1986).
43. Leiden, J. M. & Strominger, J. L. In press, Proc. Natl. Acad. Sci. U.S.A. (1986).
44. Erickson, B. W. & Merrifield, R. B. (1976) In: Neurath, H. & Hill, R. L. (eds) The proteins. Academic Press, N.Y. pp 255-527.
45. Liu, F-T, Zinnecker, M. Hamaokao, T. & Katz, D. H. Biochem. 18, 690-697 (1979).
46. Brenner, M. B., et al. (manuscript in preparation).
47. Kenneth, R. H., McKern, T. J. and Bechtol, K. B. (eds) Monoclonal Antibodies: a new dimension in biological analysis. Plenum Press, N.Y. (1980).
48. Ischimori, Y., Kurokawa, T., Honda, S., Suzuki, N., Wakimasu, M. and Tsukamoto, K., J. Immun. Method. 80, 55-66 (1985).

49. Royer, H. D., Bensussan, A., Acuto, O. and Reinherz, E. L., J. Exp. Med. 160: 947-953 (1984).
50. Acuto, O., Fabbi, M., Smart, J., Poole, C. B., Protentis, J., Royer, H. D., Schlossman, S. F. and Reinherz, E. L., Proc. Natl. Acad. Sci. U.S.A., 81, 3851-3855 (1984).
51. Maniatis T., Fritsch, E. and Sambrook, F., *Molecular Cloning, A Laboratory Manual*, Cold Spring Harbor Laboratory, Cold Spring Harbor, N.Y. 11724 (1982).
52. Schreier, M., Kohler, G., Hengartner, H., Berek, C., Trucco, M. and Formi, L., *Hybridoma Techniques*, Cold Spring Harbor Laboratory, Cold Spring Harbor, N.Y. 11724 (1980).
53. Yelton, D. E., Desaymard, C. and Scharff, M. D., Hybridoma 1, 5-11 (1981).
54. Brenner, M. B., McLean, J. and Strominger, J. L., Feb. Proc. 45, 1292 (1986).
55. Hopp, T. P., and Wood, K. R., Proc. Natl. Acad. Sci. USA 78, 3824-3828 (1981).
56. Kyte, J. and Doolittle, R. F., J. Mol. Biol. 157, 105-132 (1982).
57. Geysen, H. M., Barteling, S. J. and Meloen, R. H., Proc. Natl. Acad. Sci. U.S.A. 82, 178-182 (1985).

What is claimed is:

1. A method for detecting T cells, each of which has a δ chain of a T cell antigen receptor, which comprises contacting a sample containing T cells with an antibody capable of forming a complex with the δ chain of a T cell antigen receptor so as to form cellular complexes between the antibody and the δ chains of a T cell antigen receptor, detecting such cellular complexes and thereby detecting T cells, each of which has a δ chain of a T cell antigen receptor, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor.

2. A method of claim 1, wherein the δ chain of a T cell antigen receptor is present on the surfaces of the T cells.

3. A method of claim 1, wherein the δ chain of a T cell antigen receptor is present in the cytoplasm of the T cells.

4. A method of claim 1, wherein the antibody is capable of forming complexes with a specific δ chain of a T cell antigen receptor.

5. A method of claim 1, wherein the specific δ chain of a T cell antigen receptor is present only in suppressor T cells.

6. A method for diagnosing an immune system abnormality in a subject which comprises determining the number of T cells in a sample from the subject, contacting the sample with an antibody capable of forming a complex with at least one δ chain of a T cell antigen receptor so as to form cellular complexes between the antibody and the δ chain of a T cell antigen receptor, determining the percentage of T cells in the sample which have the δ chain of a T cell antigen receptor and comparing the percentage so determined with the percentage of T cells which have the δ chain of a T cell antigen receptor in a sample from a normal subject who does not have the immune system abnormality, a difference in the percentage of T cells so determined being indicative of the immune system abnormality, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor.

7. A method of claim 6, wherein the immune system abnormality is a cancer.

8. A method of claim 7, wherein the cancer is a leukemia.

9. A method of claim 7, wherein the cancer is a lymphoma.

10. A method of claim 6, wherein the immune system abnormality is acquired immune deficiency syndrome.

11. A method of claim 6, wherein the immune system abnormality is congenital immunodeficiency.

12. A method of claim 6, wherein the immune system abnormality is an autoimmune disease.

13. A method of claim 6, wherein the subject is an animal.

14. A method of claim 6, wherein the subject is a human.

15. A method of claim 6, wherein the sample comprises blood or tissue.

16. A method for diagnosing an immune system abnormality in a subject which comprises determining the number of T cells bearing a δ chain of a T cell antigen receptor in a sample from the subject, determining the amount of the δ chains of a T cell antigen receptor in the T cells bearing the δ chain of a T cell antigen receptor and comparing the amount so determined with the amount of the δ chains of a T cell antigen receptor in an equal number of T cells bearing the δ chain of a T cell antigen receptor in a sample from a normal subject who does not have the immune system abnormality, a difference in the amount so determined being indicative of the immune system abnormality, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor.

17. A method of claim 16, wherein the amount of a single δ chain of a T cell antigen receptor is determined.

18. A method for diagnosing an immune system abnormality in a subject which comprises:
 (a) determining in a sample from the subject the ratio of the number of T cells which have a δ chain of a T cell antigen receptor relative to the number of T cells which have a surface marker selected from the group consisting of T3, T4, T8, γ,δ T cell antigen receptor and α,β T cell antigen receptor; and
 (b) comparing the ratio of (a) to the ratio determined in a sample from a subject who does not have the immune system abnormality,
where a difference in the ratios so determined is indicative of the immune system abnormality, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor.

19. A method for detecting T cells, each of which has a γ chain of a T cell antigen receptor, which comprises contacting a sample containing T cells with an antibody capable of forming a complex with the γ chain of a T cell antigen receptor so as to form cellular complexes between the antibody and the γ chains of a T cell antigen receptor, detecting such cellular complexes and thereby detecting T cells, each of which has the γ chain of a T cell antigen receptor, in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

20. A method of claim 19, wherein the γ chain of a T cell antigen receptor is present on the surfaces of the T cells.

21. A method of claim 19, wherein the γ chain of a T cell antigen receptor is present in the cytoplasm of the T cells.

22. A method of claim 19, wherein the antibody is capable of forming complexes with a specific γ chain of a T cell antigen receptor.

23. A method of claim 22, wherein the specific γ chain of a T cell antigen receptor is present only in suppressor T cells.

24. A method for diagnosing an immune system abnormality in a subject which comprises determining the number of T cells in a sample from the subject, contacting the sample with an antibody capable of forming complexes with at least one γ chain of a T cell antigen receptor so as to form cellular complexes between the antibody and γ chains of the T cell antigen receptor, determining the percentage of T cells in the sample which have the γ chain of a T cell antigen receptor and comparing the percentage so determined with the percentage of T cells which have the γ chain of a T cell antigen receptor in a sample from a normal subject who does not have the immune system abnormality, a difference in the percentage of T cells so determined being indicative of the immune system abnormality, in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

25. A method of claim 24, wherein the immune system abnormality is a cancer.

26. A method of claim 25, wherein the cancer is a leukemia.

27. A method of claim 25, wherein the cancer is a lymphoma.

28. A method of claim 24, wherein the immune system abnormality is acquired immune deficiency syndrome.

29. A method of claim 24, wherein the immune system abnormality is congenital immunodeficiency.

30. A method of claim 24, wherein the immune system abnormality is an autoimmune disease.

31. A method of claim 24, wherein the subject is an animal.

32. A method of claim 24, wherein the subject is a human.

33. A method of claim 24, wherein the sample comprises blood or tissue.

34. A method for diagnosing an immune system abnormality in a subject which comprises determining the number of T cells bearing a γ chain of a T cell antigen receptor in a sample from the subject, determining the amount of the γ chains of a T cell antigen receptor in the T cells bearing the γ chain of a T cell antigen receptor and comparing the amount so determined with the amount of the γ chains of a T cell antigen receptor in an equal number of T cells bearing the γ chain of a T cell antigen receptor in a sample from a normal subject who does not have the immune system abnormality, a difference in the amount so determined being indicative of the immune system abnormality, in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

35. A method of claim 34, wherein the amount of a single γ chain of a T cell antigen receptor is determined.

36. A method for diagnosing an immune system abnormality in a subject which comprises:

(a) determining in a sample from the subject the ratio of the number of T cells which have a γ chain of a T cell antigen receptor relative to the number of T cells which have a surface marker selected from the group consisting of T3, T4, T8, γ,δ T cell antigen receptor and α,β T cell antigen receptor; and (b) comparing the ratio of (a) to the ratio determined in a sample from a subject who does not have the immune system abnormality, where a difference in the ratios so determined is indicative of the immune system abnormality, in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

37. A method for detecting T cells, each of which has a γ,δ T cell antigen receptor, which comprises contacting T cells with an antibody reactive with the γ,δ T cell antigen receptor so as to form cellular complexes between the antibody and the γ,δ T cell antigen receptor, detecting such cellular complexes and thereby detecting T cells, each of which has a γ,δ T cell antigen receptor, in which the δ chain of said γ,δ T cell antigen receptor (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor and in which the γ chain of said γ,δ T cell antigen receptor (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

38. A method of claim 37, wherein the γ,δ T cell antigen receptor complexes are present on the surfaces of the T cells.

39. A method of claim 37, wherein the γ,δ T cell antigen receptor complexes are present in the cytoplasm of the T cells.

40. A method of claim 37, wherein the antibody is capable of forming complexes with a specific γ,δ T cell antigen receptor complex.

41. A method of claim 40, wherein the specific γ,δ T cell antigen receptor complex is present only in suppressor T cells.

42. A method for diagnosing an immune system abnormality in a subject which comprises determining the number of T cells in a sample from the subject, contacting the sample with an antibody reactive with at least one γ,δ T cell antigen receptor so as to form cellular complexes between the antibody and the γ,δ T cell antigen receptor, determining the percentage of T cells in the sample which have the γ,δ T cell antigen receptor in a sample from a normal subject who does not have the immune system abnormality and comparing the percentage so determined with the percentage of T cells which have the γ,δ T cell antigen receptor in a sample from the normal subject who does not have the immune system abnormality, a difference in the percentage of T cells so determined being indicative of the immune system abnormality, in which the δ chain of said γ,δ T cell antigen receptor (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of said γ,δ T cell antigen receptor of the T cell antigen receptor and in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

43. A method of claim 42, wherein the immune system abnormality is a cancer.

44. A method of claim 43, wherein the cancer is a leukemia.

45. A method of claim 43, wherein the cancer is a lymphoma.

46. A method of claim 42, wherein the immune system abnormality is acquired immune deficiency syndrome.

47. A method of claim 42, wherein the immune system abnormality is congenital immunodeficiency.

48. A method of claim 42, wherein the immune system abnormality is an autoimmune disease.

49. A method of claim 42, wherein the subject is an animal.

50. A method of claim 42, wherein the subject is a human.

51. A method of claim 42, wherein the sample comprises blood or tissue.

52. A method for diagnosing an immune system abnormality in a subject which comprises determining the number of a γ,δ T cell antigen receptor bearing T cells in a sample from the subject, determining the amount of the γ,δ T cell antigen receptor in the γ,δ T cell antigen receptor bearing T cells and comparing the amount so determined with the amount of the γ,δ T cell antigen receptor in an equal number of the γ,δ T cell antigen receptor bearing T cells in a sample from a normal subject who does not have the immune system abnormality, a difference in the amount so determined being indicative of the immune system abnormality, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor and in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

53. A method of claim 52, wherein the amount of a single γ,δ T cell antigen receptor complex is determined.

54. A method for diagnosing an immune system abnormality in a subject which comprises:
(a) determining in a sample from the subject the ratio of the number of T cells which have a γ,δ T cell antigen receptor relative to the number of T cells which have a surface marker selected from the group consisting of T3, T4, T8, γ,δ T cell antigen receptor and α,β T cell antigen receptor; and
(b) comparing the ratio of (a) to the ratio determined in a sample from a subject who does not have the immune system immune system abnormality,
where a difference in the ratios so determined is indicative of the immune system abnormality, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor and in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

55. A method for detecting the presence of T cells, each of which has a δ chain of a T cell antigen receptor, which comprises contacting a sample containing T cells with an antibody capable of forming a complex with the δ chain of a T cell antigen receptor so as to form complexes between the antibody and the δ chains of a T cell antigen receptor, detecting complexes and thereby detecting the presence of T cells, each of which has the δ chain of a T cell antigen receptor, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor.

56. A method for diagnosing an immune system abnormality in a subject which comprises determining the amount of a δ chain of a T cell antigen receptor in T cells in a sample from the subject and comparing the amount so determined with the amount of the δ chain of a T cell antigen receptor in an equal number of T cells in a sample from a normal subject who does not have the immune system abnormality, a difference in the amount so determined being indicative of the immune system abnormality, in which the δ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor.

57. A method for detecting T cells, each of which has a γ chain of a T cell antigen receptor, which comprises contacting a sample containing T cells with an antibody capable of forming a complex with the γ chain of a T cell antigen receptor so as to form complexes between the antibody and the γ chains of a T cell antigen receptor, detecting such complexes and thereby detecting the presence of T cells, each of which has the γ chain of a T cell antigen receptor, in which the γ chain (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

58. A method for diagnosing an immune system abnormality in a subject which comprises determining the amount of a γ chain of a T cell antigen receptor in T cells in a sample from the subject and comparing the amount so determined with the amount of the γ chain of a T cell antigen receptor in an equal number of T cells in a sample from a normal subject who does not have the immune system abnormality, a difference in the amount so determined being indicative of the immune system abnormality, in which the γ chain (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor.

59. A method for detecting T cells, each of which has γ,δ T cell antigen receptor, which comprises contacting T cells with an antibody reactive with the γ,δ T cell antigen receptor so as to form complexes between the antibody and the γ,δ T cell antigen receptor, detecting such complexes and thereby detecting the presence of T cells, each of which has the γ,δ T cell antigen receptor, in which the δ chain of said γ,δ T cell antigen receptor (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor and in which the γ chain of said γ,δ T cell antigen receptor (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

60. A method for diagnosing an immune system abnormality in a subject which comprises determining the amount of a γ,δ T cell antigen receptor in T cells in a sample from the subject and comparing the amount so determined with the amount of the γ,δ T cell antigen receptor in an equal number of T cells in a sample from a normal subject who does not have the immune system abnormality, a difference in the amount so determined being indicative of the immune system abnormality, in which the δ chain of said γ,δ T cell antigen receptor (a) is of a form capable of being found associated in a complex with the T3 antigen on the surface of a T cell, (b) is not reactive with antibodies to the alpha or beta chain of the T cell antigen receptor, and (c) is not reactive with antibodies to the γ chain of the T cell antigen receptor and in which the γ chain of said γ,δ T cell antigen receptor (a) is of a form capable of being found associated in a complex with the T3 antigen on the surface of a T cell, (b) is not reactive with antibodies to the alpha or beta chain of the T cell antigen receptor, and (c) is reactive with an antibody to the γ chain of the T cell antigen receptor.

* * * * *